Figure 1:
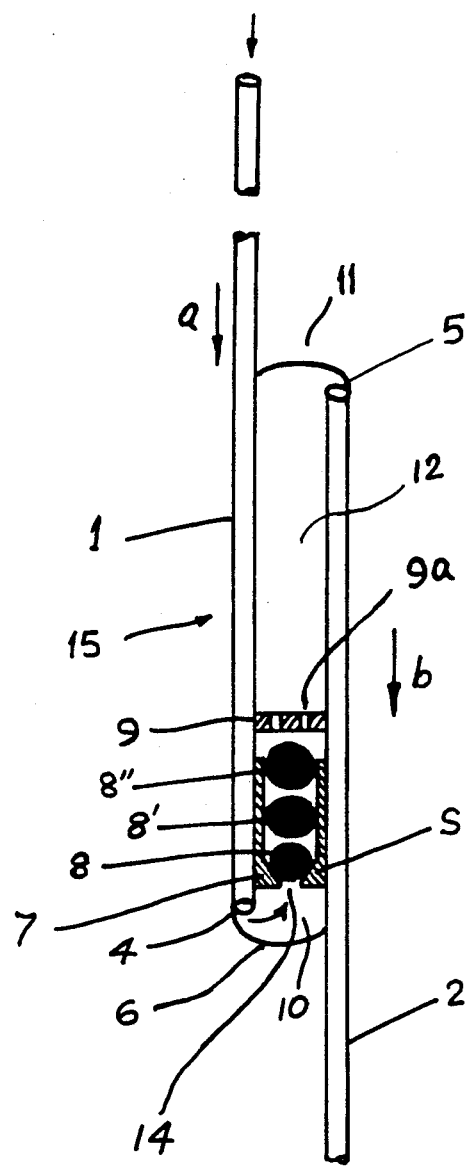

United States Patent [19]

Agarwal

[11] Patent Number: 5,042,974
[45] Date of Patent: Aug. 27, 1991

[54] SHUNT VALVE

[76] Inventor: Ghanshyam D. Agarwal, Biryagang-Shahjahanpur-242001, Uttar Pradesh, India, 242001

[21] Appl. No.: 431,732

[22] Filed: Oct. 6, 1989

[51] Int. Cl.⁵ .............................................. A61M 5/00
[52] U.S. Cl. .......................................... 604/9; 604/8; 604/247
[58] Field of Search ............................ 604/8, 9, 10, 24

[56] References Cited

U.S. PATENT DOCUMENTS

| | | | |
|---|---|---|---|
| 4,332,255 | 6/1982 | Hakim et al. | 604/9 |
| 4,551,128 | 11/1985 | Hakim et al. | 604/9 |
| 4,560,375 | 12/1985 | Shulte et al. | 604/9 |
| 4,583,967 | 4/1986 | Harris | 604/9 |
| 4,605,395 | 8/1986 | Rose et al. | 604/9 |
| 4,606,365 | 8/1986 | Siposs | 604/9 X |
| 4,636,194 | 1/1987 | Shulte et al. | 604/9 |

Primary Examiner—Robert A. Hafer
Assistant Examiner—Kerry Owens
Attorney, Agent, or Firm—B. K. Niyogi

[57] ABSTRACT

A shunt valve for draining of cerebrospinal fluid comprising a deformable housing having a proximal and distal end. A non-deformable valve chamber is disposed within the housing and such as to form an inlet chamber with the distal end and an outlet chamber with the proximal end. The shunt valve has an inlet into the inlet chamber and an outlet from the outlet chamber. The flow of the fluid within the shunt valve is a Z-flow path and the inlet and outlet are provided along the same axis.

4 Claims, 1 Drawing Sheet

SHUNT VALVE

FIELD OF INVENTION

This invention relates to a shunt valve for draining of cerebrospinal fluid and having an application for ventriculo peritoneal and ventriculo arterial shunting.

PRIOR ART

A construction of a shunt valve is known in the art for the drainage of cerebrospinal fluid. Such a valve has been described in U.S. Pat. No. 3,889,687 and comprises a housing of an elastomeric material with a first and second valve incorporated therein. The first valve is a pressure operated check valve connected in series to the second valve, which is a gravity operated ball valve. A disadvantage associated with such a valve is that means are not provided therewith for active flushing of the fluid. Yet another disadvantage is that it cannot be conveniently used for ventriculo-peritoneal and ventriculo arterial shunting. Such a shunt valve has an advantageous application only with respect to lumbo peritoneal shunting, as the valve has an effective working only when disposed along the vertical axis. If the valve is to be employed for ventriculo-peritoneal and ventriculo arterial shunting, it would then have to be disposed along the horizontal axis and in which position the valve has an ineffective application.

Such a disadvantage is avoided in another known construction of a shunt valve for drainage of cerebrospinal fluid, and which can effectively be employed for ventriculo peritoneal and ventriculo arterial shunting but not for lumbo peritoneal shunting. Such a known shunt valve has a body of deformable elastomeric material with valve means incorporated therein for control of the flow of cerebrospinal fluid. The valve means are adapted to be seated on seats provided for them at the inlet end and outlet end of the body of the shunt valve. However, a disadvantage associated with such a known construction is that means were not provided to prevent a reverse flow of the fluid on an active flushing operation. Yet another disadvantage is that the valve body could be unintentionally deformed, and thereby causing an interference in the displacement of the balls and flow of fluid.

OBJECT OF THE INVENTION

An object of this invention is to provide a shunt valve for draining cerebrospinal fluid, which valve if deformed will not flush back the fluid into the cavity around the brain.

SCOPE OF THE INVENTION

According to this invention there is provided a shunt valve for draining of cerebrospinal fluid and having an application for ventriculo peritoneal and ventriculo arterial shunting comprising a housing of a deformable elastomeric material closed at the proximal and distal ends, an inlet tube for the said fluid fixed inside the housing and opening in the proximity of the distal end of said housing, an outlet tube fixed inside the housing and having an opening at the proximal end of said housing, a non deformable valve chamber and adjacent to the distal end of the housing, said valve chamber having at one end a seat for a ball valve, a passage provided in said seat for introduction fluid within said valve chamber, and a discharge plate spaced from said seat and having a plurality of openings for discharge of the fluid from the valve chamber.

DESCRIPTION OF INVENTION WITH RESPECT TO ACCOMPANYING DRAWINGS

FIG. 1 shows schematically the shunt valve of the present invention.

The shunt valve comprises an inlet tube 1 made of a silicone plastics material, the proximal end of which is secured to a catheter (not shown) inserted into the cavity around the brain of a patient. Inlet tube 1 is secured within a housing 15 of a silicone plastics material. Housing 15 has a closed proximal end 11 and a closed distal end 6. The tube 1 has an open end 4 disposed in the proximity of the distal end 6. The cerebrospinal fluid drained into housing 15 is discharged through outlet tube 2 similar to inlet tube 1 secured within housing 15 and having an open end 5 in the proximity of proximal end 11 of housing 15.

Housing 15 has a valve chamber defined by a socket S of a rigid material e.g. stainless steel. Socket S is fixed in housing 15 and in the proximity of the distal end 6 of housing 15 and such as to define an inlet chamber 10 between in inlet end of said valve chamber and end 6. The end 4 of inlet tube 1 extends into chamber 10. Specifically socket S is disposed in the immediate proximity of end 6 so that inlet chamber has a small area so that inlet chamber 10 cannot be subjected to a flushing action. The socket S has a seat 7 at the inlet end for a ball valve 8. The valve chamber has a cover plate 9 with a plurality of holes 9a. The cover plate 9 may be integral with socket S. Alternatively, the cover plate 9 may be separate from socket S and fixed within housing 15. The cover plate 9 is provided at the outlet end of the valve chamber and disposed away from the proximal end 11 of housing 15 and such as to define an outlet chamber 12 with a substantial area so as to allow an active flushing operation. Thus, and as by way of a typical example, the total length of housing 15 may be 42 mm with an outlet chamber of 23 mm length and inlet chamber of 2 mm length.

The outlet tube 2 is led to the left artrium of the heart or peritoneal cavity of the patient, through a distal catheter 3 fixed to its end.

If desired one, two or more ball valves 8', 8" may be provided in the socket S, in addition to the ball valve 8.

Housing 15 and tubes 2, 3 are embedded below the skin of the patient after the proximal and the distal catheters are inserted as already explained. The cerebrospinal fluid flows through the inlet tube 2 in the direction of arrow 'a' and drains into chamber 15 through its open end 4. The fluid flows through passage 14 in the valve seat 7 of the socket S and exerts a force on ball 8 and such as to displace 8 away from said passage and allow the fluid to flow towards plate 9. The fluid then enters outlet chamber 12 and flows through the open end 5 of the tube 2 in the direction of arrow b and through the catheter 3 into the left artrium or peritoneal cavity of the patient and excreated therefrom.

Housing 15 of the shunt valve is vertical, horizontal or inclinded depending on the posture of the patient. If an active flushing action is required, pressure is applied to the deformable part of the valve, namely outlet chamber 12, so that the fluid flows only in the direction of arrow 'b' and through tube 2. Simultaneously, and in such an active flushing action, the fluid cannot flow back into tube 1 and the cavity around the brain as the ball valve 8 will be forced on the seat 7 and close the hole in the valve seat. The valve chamber cannot be deformed as socket S is rigid. Simultaneously, the available are for a pumping action is only that of outlet chamber 12, which further ensures that the fluid cannot have a reverse flow into tube 1.

Accordingly, only the outward flushing of said fluid into tube 2 is ensured and return flow of the fluid in tube 1 is prevented. In any normal position of the body 6, the ball valves 8,8' and 8" are supported by the cover plate 9 which prevent their falling off into outlet chamber 12, holes 9a in the plate 9 free flow of the fluid therethrough. Furthermore, a plate 9 with holes 9a is provided rather than a seat 4 at the opposite end of the valve chamber to ensure a flow of the fluid after an active flushing action. If seat 4 was provided rather than plate 9, the opening in seat 4 would be closed by the balls and thereby prevent a flow of the fluid into outlet chamber 12 immediately after an active flushing operation.

In the construction of the valve of present invention, the fluid has a Z form of flow.

I claim:

1. A shunt valve for draining of cerebrospinal fluid and having an application for ventricule peritoneal and ventriculo arterial shunting comprising a housing of a deformable elastomeric material closed at the proximal and distal ends, a non-deformable valve chamber adjacent to the distal end of the housing, said valve chamber having an inlet at one end and an outlet at the opposite end, an inlet chamber provided between the inlet end of said valve and the distal end of said housing, a deformable outlet chamber provided between the outlet of said valve and the proximal end of the housing, an inlet tube for the said fluid and extending along one of the longitudinal sides of said housing and opening into the inlet chamber, an outlet tube extending along a longitudinal side of said housing and opposite to that of the inlet tube and having an opening in the outlet chamber, said valve chamber having at the inlet end a seat for a ball valve and a discharge plate at the outlet end, a passage provided in said seat for introduction of fluid within said valve chamber, the discharge plate for regulating discharge at the outlet end provided with a plurality of spaced openings cooperating with the ball valve for discharge of the fluid from the valve chamber even after an active flushing of said valve, said inlet and outlet tubes disposed along the same axis.

2. A shunt valve as claimed in claim 1 wherein said valve chamber comprises a socket of a rigid material.

3. A shunt valve as claimed in claim 1 wherein the fluid flow is adapted to a Z-flow path within said valve.

4. A shunt valve as claimed in claim 1 wherein the inlet chamber has an area smaller than that of the outlet chamber so as to prevent an active flushing operation.

* * * * *